(12) United States Patent
Edwards

(10) Patent No.: US 6,452,389 B1
(45) Date of Patent: Sep. 17, 2002

(54) NMR PULSE SEQUENCES FOR INCREASING THE EFFICIENCY OF ACQUISITION

(75) Inventor: Carl M. Edwards, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 29 days.

(21) Appl. No.: 09/778,554

(22) Filed: Feb. 7, 2001

(51) Int. Cl.[7] .................................................. G01V 3/00
(52) U.S. Cl. ...................................... 324/303; 324/309
(58) Field of Search .................................. 324/303, 300, 324/306, 307, 309, 310, 312, 314, 318, 322

(56) References Cited

U.S. PATENT DOCUMENTS

| | | | |
|---|---|---|---|
| 4,832,037 A | 5/1989 | Granot | 128/653 |
| 5,412,320 A | 5/1995 | Coates | 324/303 |
| 5,451,873 A | 9/1995 | Freedman et al. | 324/303 |
| 5,486,762 A | 1/1996 | Freedman et al. | 324/303 |
| 5,497,087 A | 3/1996 | Vinegar et al. | 324/303 |
| 5,557,200 A | 9/1996 | Coates | 324/303 |
| 5,596,274 A | 1/1997 | Sezginer | 324/303 |
| 5,936,405 A | 8/1999 | Prammer et al. | 324/303 |
| 6,005,389 A | 12/1999 | Prammer | 324/303 |
| 6,049,205 A | 4/2000 | Taicher et al. | 324/303 |
| 6,140,817 A | 10/2000 | Flaum et al. | 324/303 |
| 6,163,153 A | 12/2000 | Reiderman et al. | 324/314 |
| 6,344,744 B2 * | 2/2002 | Taicher et al. | 324/300 |
| 6,377,042 B1 * | 4/2002 | Menger et al. | 324/303 |

OTHER PUBLICATIONS

K–J Dunn, et al.; *A Method for Inverting NMR Data Sets with Different Signal to Noise Ratios*, SPWLA 39th Annual Logging Symposium, May 26–29, 1998, pp. 1–11.

M.G. Prammer, et al.; *Measurements of Clay–Bound Water and Total Porosity by Magnetic Resonance Logging*, SPE 36522, pp. 311–320.

Keh–Jim Dunn, et al.; *The Inversion of NMR Log Data Sets with Different Measurement Errors*, Journal of Magnetic Resonance 140, 1999, pp. 153–161.

Kenneth P. Whittall, et al.; *Quantitative Interpretation of NMR Relaxation Data*, Journal of Magnetic Resonance 84, 1989, pp. 134–152.

* cited by examiner

*Primary Examiner*—Louis Arana
(74) *Attorney, Agent, or Firm*—Madan, Mossman & Sriram, P.C.

(57) ABSTRACT

A plurality of CPMG sequences is used to obtain NMR data with an instrument having a gradient magnetic with a constant resolution of $T_2$. Different values of acquisition time (AT) are used for different frequencies with a typical ratio of the number of frequencies having a given AT being 1:1:2:4:8 with a corresponding ratio of ATs of 16:8:4:2:1. In an alternate embodiment of the invention, modified CPMG sequences are used wherein the angle associated with the refocusing pulses is less than 180°.

22 Claims, 4 Drawing Sheets

NMR PULSE SEQUENCES FOR INCREASING THE EFFICIENCY OF ACQUISITION

FIELD OF THE INVENTION

The invention is related to the field of electromagnetic well logging instruments and methods. More specifically, the invention is related to the use of NMR pulse sequences for improving the efficiency of nuclear magnetic resonance ("NMR") well logging data acquisition.

BACKGROUND OF THE INVENTION

Electromagnetic well logging instruments include circuits connected to antennas which induce alternating electromagnetic fields in earth formations surrounding a wellbore, and include circuits which measure various electromagnetic phenomena which occur as a result of interaction of the alternating electromagnetic fields with the earth formations. Such electromagnetic phenomena relate to petrophysical properties of interest of the earth formations. One type of electromagnetic well logging instrument that suffers deleterious effects of eddy currents in electrically conductive elements of the logging instrument is the nuclear magnetic resonance ("NMR") instrument.

An apparatus described in U.S. Pat. No. 4,710,713 issued to Taicher et al is typical of NMR instruments used to measure certain petrophysical properties of earth formations from within a wellbore drilled through the earth formations. NMR well logging instruments such as the one disclosed by Taicher et al typically include a magnet for polarizing nuclei in the earth formations surrounding the wellbore along a static magnetic field, and at least one antenna for transmitting radio frequency ("RF") energy pulses into the formations. The RF pulses reorient the spin axes of certain nuclei in the earth formations in a predetermined direction. As the spin axes precessionally rotate and reorient themselves into alignment with the static magnetic field, they emit RF energy that can be detected by the antenna. The magnitude of the RF energy emitted by the precessing nuclei, and the rate at which the magnitude changes are related to certain petrophysical properties of interest in the earth formations.

There are several principal operating parameters in NMR well logging which should be optimized for efficient operation of an NMR well logging instrument. These parameters include the logging speed (speed of motion of the instrument along the wellbore), the average and the peak power supplied to the instrument and transmitted as RF pulses, and the signal-to-noise ratio ("SNR"). Other parameters of interest include the vertical resolution of the instrument and the radial depth of investigation of the measurements made by the instrument within the formations surrounding the wellbore. The last two of these parameters are primarily determined by the antenna and magnet configurations of the NMR logging instrument. Improvements to these two parameters are the subject of numerous patents and other publications. Providing more flexibility in the instrument's peak power requirements, and limitations on the logging speed necessitated by the physics of NMR measurement have been more difficult to overcome.

A property of NMR measurements made in porous media such as earth formations is that there is typically a significant difference between the longitudinal relaxation time $T_1$ distribution and the transverse relaxation time $T_2$ distribution of fluids filling the pore spaces of the porous medium. For example, light hydrocarbons and natural gas, as commonly are present in the pore spaces of some earth formations, may have $T_1$ relaxation times as long as several seconds, while the $T_2$ relaxation times may be only about 1/100 that amount. This aspect of NMR well logging is due primarily to the effect of diffusion occurring within static magnetic field amplitude gradients. These amplitude gradients can arise from the inhomogeneous applied static magnetic field or from the earth formations itself. The latter gradients are caused by differences in magnetic susceptibility between the solid portion of the earth formation (referred to as the rock "matrix") and the fluid filling the pore spaces.

In order to perform precise NMR measurements on any medium, including earth formations, the nuclei of the material should be polarized by the static magnetic field for about 5 times the longest $T_1$ relaxation time of any individual component within the material. This is generally not the case for well logging NMR measurements, since some formation components, as previously explained, may have $T_1$ relaxation times as long as several seconds (requiring a polarization time of as long as about 30 seconds). This is such a long polarization time as to make impracticable having enough polarization time at commercially acceptable logging speeds. As the instrument moves along the wellbore, the earth formations that are subject to the static magnetic field induced by the instrument are constantly changing. See for example, "An Experimental Investigation of Methane in Rock Materials," C. Straley, SPWLA Logging Symposium Transactions, paper AA (1997).

As a result of logging speed considerations, a polarization time of 8 to 10 seconds has become more common for many NMR well logging procedures, including those used for natural gas detection. See for example, "Selection of Optimal Acquisition Parameters for MRIL Logs," R. Akkurt et al, The Log Analyst, Vol. 36, No. 6, pp. 43–52 (1996).

Typical NMR well logging measurement procedures include transmission of a series of RF energy pulses in a Carr-Purcell-Meiboom-Gill ("CPMG") pulse sequence. For well logging instruments known in the art, the CPMG pulse sequences are about 0.5 to 1 seconds in total duration, depending on the number of individual pulses and the time span ("TE") between the individual RF pulses. Each series of CPMG pulses can be referred to as a "measurement set".

In the typical NMR well logging procedure only about 30 percent of the total amount of time in between each NMR measurement set is used for RF power transmission of the CPMG pulse sequence. The remaining 60 percent of the time is used for polarizing the earth formations along the static magnetic field. Further, more than half of the total amount of time within any of the CPMG sequences actually takes place between individual RF pulses, rather than during actual transmission of RF power. As a result of the small fractional amount of RF transmission time in the typical NMR measurement sequence, the RF power transmitting components in the well logging instrument are used inefficiently on a time basis. In well logging applications this inefficiency can be detrimental to the overall ability to obtain accurate NMR measurements. The signal-to-noise per unit time is proportional to square root of the average RF power used. Because the amount of electrical power which can reasonably be supplied to the NMR logging instrument (some of which, of course, is used to generate the RF pulses for the NMR measurements) is limited by the power carrying capability of an electrical cable which is used to move the logging instrument through the wellbore, inefficient use of the RF power on a time basis results in measurements with poor spatial resolution or unacceptable logging speeds.

Several methods are known in the art for dealing with the problem of non-transmitting time in an NMR measurement set. The first method assumes a known, fixed relationship between $T_1$ and $T_2$ as suggested for example, in "Processing of Data from an NMR Logging Tool," R. Freedman et al, Society of Petroleum Engineers paper no. 30560 (1995). Based on the assumption of a fixed relationship between $T_1$ and $T_2$, the waiting (repolarization) time between individual CPMG measurement sequences is shortened and the measurement results are adjusted using the values of $T_2$ measured during the CPMG sequences. Disadvantages of this method are described, for example in, "Selection of Optimal Acquisition Parameters for MRIL Logs," R. Akkurt et al, The Log Analyst, vol. 36, no. 6, pp. 43–52 (1996). These disadvantages can be summarized as follows.

First, the relationship between $T_1$ and $T_2$ is not a fixed one, and in fact can vary over a wide range, making any adjustment to the purported $T_1$ measurement based on the $T_2$ measurements inaccurate at best. Second, in porous media $T_1$ and $T_2$ are distributions rather than single values. It has proven difficult to "adjust" $T_1$ distributions based on distributions of $T_2$ values.

Another method known in the art for increasing the power efficiency of an NMR well logging instrument is described, for example in, "Improved Log Quality with a Dual Frequency Pulsed NMR Tool," R. N. Chandler et al, Society of Petroleum Engineers paper no. 28365 (1994). The Chandler et al reference describes using large downhole capacitors to store electrical energy during the waiting (repolarization) time and then using high peak-power during application of the RF pulses in the CPMG sequences to improve the signal-to-noise ratio ("SNR"). There are several disadvantages to the method described in the Chandler et al reference. First, it is very expensive to have large capacitors in a well logging instrument, which must be able to operate at high temperature (generally in excess of 180° C.). Second, using high peak RF power to improve SNR involves complicated and expensive transmitter switching circuits. The switching circuit design problem is only made worse by the requirement that the well logging instrument be able to withstand 180° C. or more. Using high peak power is also not very effective for the purpose of improving SNR because the SNR increases only as the fourth root of the increase in the peak RF pulse power.

Another NMR logging apparatus, known as the Combinable Magnetic Resonance ("CMR") logging tool, is described in U.S. Pat. No. 5,432,446 issued to MacInnis et al. The CMR logging tool includes permanent magnets arranged to induce a magnetic field at two different lateral distances along the wellbore and at two different radial depths of investigation within the earth formation. Each depth of investigation has substantially zero magnetic field amplitude gradient within a predetermined sensitive volume. The objective of apparatus disclosed in the MacInnis patent is to compare the output indications from the first and the second sensitive volumes to determine the effects of borehole fluid "invasion" on the NMR measurements. A drawback to the CMR tool, however, is that both its sensitive volumes are only about 0.8 cm away from the tool surface and extend only to about 2.5 cm radially outward from the tool surface into the earth formation. Measurements made by the CMR tool are subject to large error caused by, among other things, roughness in the wall of the wellbore, by deposits of the solid phase of the drilling mud (called "mudcake") onto the wall of the wellbore in any substantial thickness, and by the fluid content of the formation in the invaded zone.

In NMR well logging measuring techniques, reducing the so called "dead time" (the time between an initial 90° RF pulse and a first one of the 180° rephasing pulses in the CPMG sequence) during which no spin-echo measurements are made due to "ringing" of the antenna in the static magnetic field) is important in order to be able to resolve the presence of earth formation components having very short $T_2$ times. As the dead time is reduced, it becomes necessary in a CPMG pulse sequence to reduce the amount of time ("TE") between individual 180° rephasing pulses in the CPMG sequence. Some devices, such as one described in "Measurement of Total NMR Porosity Adds New Value to NMR Logging", R. Freedman et al, SPWLA Logging Symposium Transactions, paper OO (1997), have achieved a time-to-first-echo (and subsequent TE) of as short as 0.2 milliseconds (msec). Since the expected $T_2$ distribution of typical earth formations extends to one second or more, however, a CPMG measurement sequence of at least 1 sec total length is required to measure the petrophysical properties of typical earth formations. The result of the combination of the need to measure very short and very long $T_2$ relaxation time components results in an CPMG measurement sequence including 8,000 or more echoes ("echo train") using instruments such as the CMR.

Most petrophysical parameters of interest such as irreducible water saturation, fractional volume of movable ("free") fluid, permeability, etc. are based on only one differentiation between "short" (defined as between 0 and about 33 msec) and "long" defined as more than about 33 msec) parts of the $T_2$ distribution. Assuming the CPMG pulse sequence (and resulting "echo train") is about 1 sec in duration, only about 3 percent of the total duration of the echo train is substantially sensitive to components of the earth formation having short $T_2$ values, as compared to about 97 percent of the echo train being substantially sensitive to components of the earth formation having long $T_2$ values. The nature of the typical echo train therefore results in stable, precise values for parameters such as the fractional volume of free fluid ("FFI"), but can result in unsatisfactory stability and precision in the values determined for other petrophysical properties such as the irreducible water saturation ("BVI"). See, for example, "Improved Log Quality with a Dual-Frequency Pulsed NMR Tool," R. N. Chandler et al, Society of Petroleum Engineers paper no. 28365 (1994).

A method for increasing the time efficiency of NMR pulsing sequences is described in U.S. Pat. No. 4,832,037 issued to Granot. The method described in Granot includes applying a static magnetic field to materials to be analyzed, momentarily applying a gradient field to the materials to be analyzed, and applying an RF pulse to an antenna at a first frequency to transversely polarize the nuclei of the material within a specific geometric region. The specific geometric region is the location at which the total magnetic field strength, which is the sum of the static field and the gradient field, corresponds to the Larmor frequency of the polarized nuclei within the specific geometric region. After the gradient field is switched off, the free induction decay ("FID") signal is measured and spectrally analyzed. During a waiting time, generally about equal to $T_1$, between successive magnetic resonance experiments in the same specific geometric region, additional gradient pulses and RF pulses at different frequencies can be applied to measure the FID signal from different geometric regions within the materials to be analyzed. By measuring the FID signal from within different geometric regions during the waiting time, a plurality of different regions in the materials can be analyzed substantially in the same time span as needed to analyze a single geometric region within the materials. The method in Granot is not useful for well logging, however. First, using gradient pulses as needed for the Granot technique would dramatically increase the power consumption of the well logging instrument. Since the power carrying capacity of the well logging cable is limited, it is not preferred to have additional uses of power in the well logging instrument such as energizing gradient coils. Second, the method in Granot is intended primarily for measurements of the FID signal, rather than measurements of spin echo amplitude decay and $T_2$ as is more typical of well logging techniques. Using momentary gradient fields superimposed on the static magnetic field would make it difficult to measure spin echo amplitude decay and $T_2$ since the polarized nuclei in earth formations in any spatial volume would not have an opportunity to return to magnetic equilibrium between successive measurements made according to the technique disclosed in Granot.

U.S. Pat. No. 6,049,205 to Taicher et al. ("Taicher '205") teaches a method for determining the nuclear magnetic resonance longitudinal relaxation time $T_1$ of a medium. The method includes magnetically polarizing nuclei in the medium along a static magnetic field. The nuclei are momentarily inverted as to their magnetic polarization within each one of a plurality of different spatial volumes within the medium. The inversion is performed by transmitting a series of 180° pulses each at a frequency corresponding to the static magnetic field strength within each sensitive volume. The nuclei in each sensitive volume are then transversely magnetized after an individual recovery time corresponding to each one of the spatial volumes. The amplitude of a magnetic resonance signal from each one of the spatial volumes is measured in order to calculate the $T_1$ relaxation curve. The transverse magnetization is induced in each one of the individual sensitive volumes by transmitting radio frequency pulses at frequencies corresponding to the static magnetic field strength within each sensitive volume. In the preferred embodiment, the transverse magnetization is performed by transmitting a series of CPMG "read-out" pulse sequences, each sequence transmitted at a frequency corresponding to each one of the sensitive volumes, and including measuring the amplitude of the resulting spin echoes in each CPMG sequence.

Taicher '205 determines the transverse relaxation time distribution of the medium with an improved signal-to-noise ratio. The medium is polarized along a static magnetic field. A first CPMG echo train is acquired from within a first sensitive volume. The first CPMG train has an inter-echo spacing and a duration large enough to determine the presence of slowly relaxing components in the medium. Then a plurality of additional CPMG echo trains is acquired. Each of the additional echo trains corresponds to a different sensitive volume, and each of the additional CPMG echo trains has an inter-echo spacing and a duration less than the duration and echo spacing of the first CPMG echo train. Different sensitive volumes are measured by transmitting each additional CPMG sequence at a different radio frequency. In the preferred embodiment, the additional echo trains have a duration and inter-echo spacing adapted to determine the presence of components in the formation having a transverse relaxation time less than about 33 milliseconds. The total duration of all the additional echo trains is about equal to the duration of the first echo train. In the preferred embodiment, the total radio frequency power transmitted in the all the additional echo trains is approximately equal to the radio frequency power transmitted in the first echo train.

Implicit in the teachings of Taicher '205 is the assumption that the diffusion relaxation time is much less than any $T_2$ component in the spectra. This requirement can only be satisfied under limited conditions. The magnetic field gradient must be small (less than 10 G/cm), or the inter-echo spacing TE must be very short or the diffusion constant must be small. The first two conditions are design criteria for a logging tool, while the last condition is a requirement of formation properties that may not necessarily be satisfied. None of the commercial tools in use today are designed to satisfy either the gradient condition or the TE requirement. Some designs that have been suggested satisfy these conditions but require that the reservoir have large pores, heavy oil or a low temperature; these suggested designs cannot function properly if the reservoir contains gas.

The present invention has none of these requirements and only requires that the wait time be sufficiently long to polarize the formation fluids. This condition is the same as in prior art $T_2$ acquisition.

SUMMARY OF THE INVENTION

The present invention is a multi-frequency method of obtaining NMR data using CPMG sequences having different durations such that the resulting data have substantially uniform resolvability of the $T_2$ distribution. The acquisition time (AT) of the later echo trains is shortened relative to the earlier echo trains with the product of the AT and the number of echo trains having a selected AT being kept substantially constant. The echo time (TE) is kept constant for all the echo trains. The wait time (TW) is either much greater than the largest formation fluid spin-lattice relaxation time or is also kept constant.

DESCRIPTION OF THE PREFERRED EMBODIMENT

An NMR well logging apparatus which is suitable for use with this invention is described, for example, in U.S. Pat. No. 5,712,566 to Taicher et al ("Taicher '566"). The apparatus described in Taicher '566 includes a magnet for inducing a static magnetic field in the earth formations. The static magnetic field includes an amplitude gradient directed radially inwardly towards the longitudinal axis of the instrument. The apparatus disclosed in Taicher '566 includes an antenna through which pulses of RF power are conducted to excite nuclei of the earth formations surrounding the instrument. The antenna includes a wire coil wound around a high magnetic permeability ferrite. The ferrite includes a frequency control coil wound thereon. By passing a selectively controllable DC voltage through the frequency control coil, the tuning frequency of the antenna can be selectively controlled, making transmission and reception of RF energy at the selected frequency. The apparatus disclosed in Taicher '566 can make NMR measurements at a plurality of different frequencies. Since the static magnetic field imparted by the magnet disclosed in Taicher '566 includes an amplitude gradient, conducting NMR measurements at different frequencies will result in these different frequency NMR measurements taking place in different sensitive (excitation) volumes.

It is to be clearly understood that the apparatus disclosed Taicher '566 is not the only apparatus that can be used for this invention. For purposes of this invention it is only necessary that the NMR apparatus be able to selectively excite different sensitive volumes to nuclear magnetic resonance, and selectively receive NMR signals from each of the selectively excited sensitive volumes. Using multiple frequencies for individual NMR measurement sequences in a gradient static magnetic field is a particularly convenient means by which to carry out the method of this invention, and so the apparatus disclosed in Taicher '566 is a particularly convenient instrument, but not the exclusive instrument by which to carry out the method of this invention.

Figure 1:
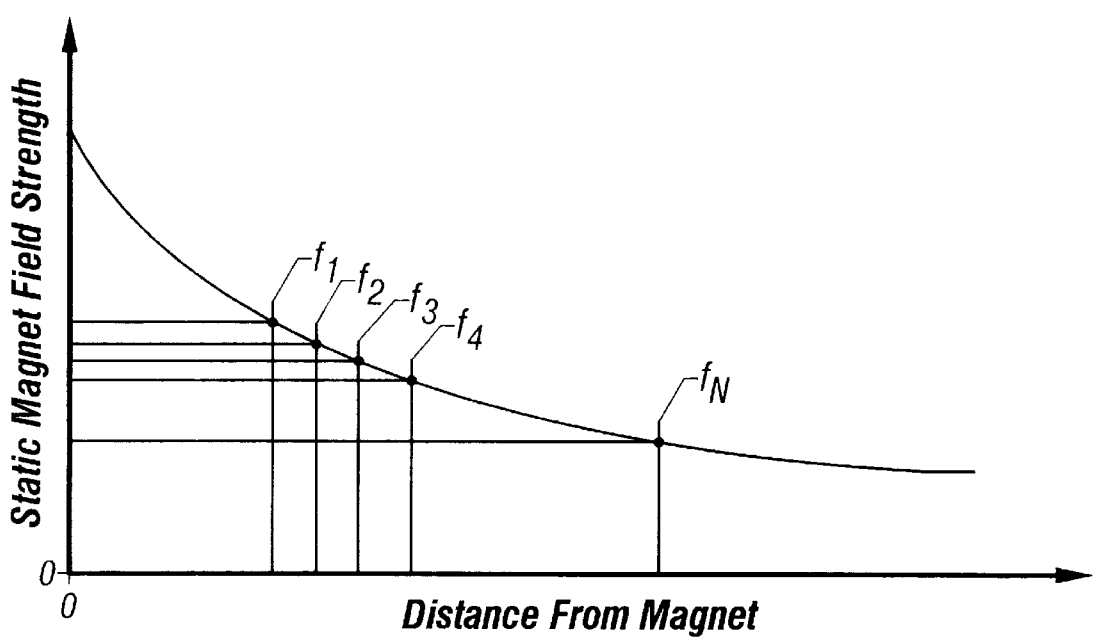
FIG. 1 shows a graph of amplitude of the static magnetic field of the magnet in a gradient NMR well logging apparatus used with the invention.

FIG. 1 shows a graph of the amplitude of the static magnetic field, with respect to distance from the magnet, for the well logging apparatus described in Taicher '566. The amplitude of the static magnetic field generally decreases with respect to the lateral distance from the magnet. As is well known in the art, nuclear magnetic resonance conditions occur when a radio frequency magnetic field is applied to materials polarized along a static magnetic field where the frequency of the RF magnetic field matches the product of the static magnetic field strength and the gyromagnetic ratio of the nuclei being polarized by the static magnetic field, this product being referred to as the Larmor frequency. As can be inferred from the graph in FIG. 1, by adjusting the frequency of the RF magnetic field, the distance from the magnet at which nuclear magnetic resonance conditions occur can be changed corresponding to the static magnetic field amplitude at that particular distance from the magnet. For example, if frequency $f_1$ is the highest frequency, resonance will occur at the smallest distance to the magnet, and so on through lower frequencies $f_2$ through $f_N$. Because nuclear magnetic resonance only occurs where the static magnetic field strength matches the RF magnetic field frequency, nuclear magnetic resonance measurements can be conducted within a number of different non-overlapping sensitive volumes by inducing nuclear magnetic resonance at different frequencies. A particular set of non-overlapping sensitive volumes which would result when using the apparatus described in Taicher '566, for example, would comprise thin annular cylinders each having an average radius corresponding to the particular static magnetic field amplitude in which nuclear magnetic resonance would occur at a particular RF magnetic field frequency. The thickness of each annular cylinder would be related to the bandwidth the bandwidth of the transmitted RF pulses, the bandwidth of a receiver circuit in the NMR instrument and the rate at which the static magnetic field changes in amplitude.

This feature of the static magnetic field, and the selectable frequency capability for the RF magnetic field in the apparatus described in Taicher '566 makes it possible to conduct time-overlapping NMR measurements within different sensitive volumes. By time-overlapping NMR experiments in different sensitive volumes, it is possible to more efficiently use the RF transmitting components in the apparatus. The manner in which the RF transmitting components are used more efficiently will now be explained.

Most current state-of-the-art NMR logging techniques can be classified as "constant acquisition time" acquisitions. What is meant by "constant acquisition time" is that the acquisition time, AT, for all the pulse sequences that comprise an acquisition is constant. It is true for the standard $T_2$ acquisition, the bound water acquisition, and the differential spectrum methods. The single exception to this generalization is the "Clay-bound water" acquisition.

Given a multi-frequency tool that is capable of continuous pulsing, Granot teaches that the number of frequencies needed is given by $$N=TR/AT=1+TW/AT, \qquad (1)$$

where N is the number of frequencies, $T_R$ is the repetition time, and $T_W$ is the wait time. With such a choice of the parameters, the wait time for one frequency is completely filled with experiments at other frequencies, and continuous pulsing is achieved.

Figure 2:
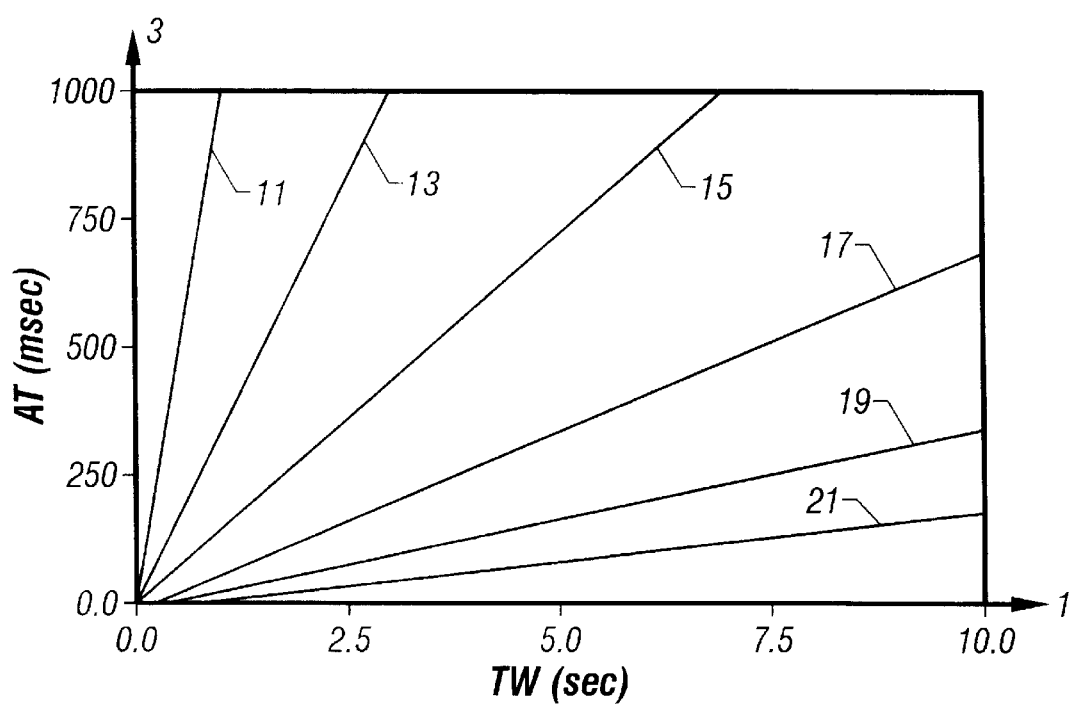
FIG. 2 shows the maximum number of frequencies, N, for a standard $T_2$ acquisition, given $T_W$ and $A_T$.

The number of frequencies is dependent on the choice of $T_W$ and AT Thus, N depends on the formation fluid properties. Referring now to FIG. 2, the maximum acquisition time possible for a given $T_W$ and a given number of frequencies is shown. The abscissa 1 is the wait time $T_W$ and the ordinate 3 is the acquisition time AT. The curves 11, 13, 15, 17, 19 and 21 correspond to 2, 4, 8, 16, 32 and 64 acquisition frequencies respectively. It can be seen from FIG. 2 that for an acquisition time AT of 1000 msec and a wait time $T_W$ of 9 sec, only 10 frequencies are needed.

For a constant acquisition time, when N is less than the number of frequencies (or sensitive volumes), $N_T$, available, the Signal to Noise ratio (SNR) and $T_2$ spectrum resolvability suffer. First, consider the SNR per root time, snr, for the initial echo using a standard $T_2$ acquisition. For a single frequency tool $$snr = \frac{SNR_0 \sqrt{N_a}}{\sqrt{N_a TR}} = \frac{SNR_0}{\sqrt{TR}}, \qquad (2)$$

where $N_a$ is the number of echoes averaged together. Eq. (2) shows that the snr is independent of $N_a$ and can be improved by decreasing $T_R$. However, the repetition time $T_R$ is fixed by the spin-lattice relaxation times of the formation fluids, so that for a given formation fluid, snr is also fixed. For a multi-frequency tool, $N_a$ is the product of number of frequencies N and the number of echoes averaged at each frequency $N_{af}$. Thus $$snr = \frac{SNR_0 \sqrt{N_a}}{\sqrt{N_{af} TR}} = SNR_0 \sqrt{\frac{N}{TR}} \qquad (3)$$
$$= \frac{SNR_0}{\sqrt{AT}}.$$

Eq. (3) shows that the snr is increased by the square root of the number of frequencies compared to a single frequency acquisition. When continuous pulsing is used, eq. (1) when combined with eq. (3) gives the result that the snr is fixed because AT, like $T_W$ is fixed by the formation fluid properties.

In the present invention, the acquisition is altered to make use of all frequencies available from the tool. This gives an SNR per root time of $$snr' = SNR_0 \sqrt{\frac{N_T}{TR}}. \quad (4)$$

and the increase in snr relative to a fixed AT continuous pulsing acquisition is given by $$\frac{snr'}{snr} = \sqrt{\frac{N_T}{N}} \quad (5)$$

Doubling the number of frequencies in an acquisition will increase snr by 41%. N is determined for formation fluid properties and not by tool specifications so that improvements could be realized. The present invention describes a class of acquisitions that increases the number of frequencies used relative to constant AT acquisitions.

To accurately obtain an estimate of a long $T_2$, one would like to make to let $AT \approx 3T_2$. Most light oils have an apparent $T_2$ between 500 to 600 msec and a $T_1$ of 3–4 seconds. Thus, in the ideal case, we would want an AT=1.5 sec and a $T_W$ of 12 sec. From eq. (1) using a fixed AT and continuous pulsing would require nine frequencies for a standard $T_2$ log, but the snr could be improved by 33% with a 16-frequency tool or 15% with a 12-frequency tool (from eq. 5).

In order to understand the conditions under which this improvement in snr can be realized for continuous pulsing in a multi-frequency tool, we should attempt to quantify how AT and $T_W$ are selected given the formation NMR parameters. First, the engineer selects a $T_W$ so that the formation is nearly polarized just prior to the pulse sequence at the same frequency. $T_W$ is selected to be some multiple of the maximum spin-lattice relaxation time $T_{1max}$.

$$TW = c_1 T_{1max} \quad (6)$$

where $c_1$ is a constant. When $c_1=3$, then the formation is 95% polarized while a value of $c_1$ greater than or equal to 5 results in a polarization of the medium within 1% of the maximum. This is the ideal situation. In practice, to keep the acquisition time manageable, $c_1$ is usually around 3.

Next, the acquisition time AT is selected. Ideally, the acquisition time would be selected so that the echo train has reached the baseline: if AT is greater, then the data only provides information about the baseline and not about the $T_2$ spectrum. If AT is too small, then the resolution of the spectral components for large values of $T_2$ will suffer. Accordingly, AT is set to a value that is a multiple of the maximum transverse relaxation time $T_{2max}$ as $$AT = c_2 T_{2max}, \quad (7)$$

where $c_2$ is between 1.0 and 3.0. A value of $c_2$ close to 1 will reduce the resolvability of long $T_2$ components.

The number of frequencies that optimizes the standard fixed AT logging mode is then dictated by the formation properties $$N = 1 + TW/AT \quad (8)$$
$$= 1 + \frac{c_1}{c_2}\left(\frac{T_{1max}}{T_{2max}}\right)$$
$$= 1 + k\left(\frac{T_{1max}}{T_{2max}}\right),$$

where k is between 1.6 and 3.0.

The ratio $T_{1max}/T_{2max}$ is dependent upon the fluid and rock properties. Table I shows ranges of $T_1$ and $T_2$ for typical formation fluids in reservoir rocks.

TABLE I

Estimation of maximum relaxation times for formation fluids.

| Quantity | Light Oil $T_2 \ll T_1$ | Medium Oil $T_2 \approx T_1$ | Heavy Oil $T_2 = T_1$ | Gas $T_2 \ll T_1$ | Water Sandstone $T_2 \approx T_1$ | Water Limestone $T_2 \approx T_1$ |
|---|---|---|---|---|---|---|
| $T_{1max}$ | 2–8 sec. | 0.1–2.0 | <0.1 | 3.0–5.0 | .375–.6 | .5–.9 |
| $T_{2max}$ | 0.4–0.8 | 0.1–0.6 | <0.1 | 0.008–0.06 | 0.25–0.40 | 0.33–0.60 |
| $T_{1max}/T_{2max}$ | 5–10 | 1.0–3.33 | 1 | 100–200 | ≈1.5 | ≈1.5 |

It is the combination of fluids in the formation that dictates the maximum relaxation times. Water is usually thought to wet the surface, so it is always present in the formation. To estimate the number of frequencies that maximizes snr, the values in TABLE I must be combined, as shown in TABLE II.

TABLE II

Estimation of maximum relaxation properties and number of frequencies to optimize standard $T_2$ acquisition

| Lithology | Water/gas | Water/light oil | Water/medium oil | Water/heavy oil |
|---|---|---|---|---|
| $T_{1max}$ | | | | |
| Sandstone | 3–5 | 2–8 | .375–2 | .375–6 |
| Carbonate | 3–5 | 2–8 | .5–2 | .375–6 |
| $T_{2max}$ | | | | |
| Sandstone | .1–.25 | .4–.8 | .25–.6 | .25–.4 |
| Carbonate | .1–.6 | .4–.8 | .1–.6 | .25–.4 |

TABLE II-continued

Estimation of maximum relaxation properties and number of frequencies to optimize standard $T_2$ acquisition

| Lithology | Water/gas | Water/light oil | Water/medium oil | Water/heavy oil |
|---|---|---|---|---|
| $T_{1max}/T_{2max}$ | | | | |
| Sandstone | 12–50 | 2.5–10 | 1.5–3.3 | ≈1.5 |
| Carbonate | 5–50 | 2.5–10 | 3.3–5 | ≈1.5 |
| $N_f$ | | | | |
| Sandstone | 25–100 | 6–21 | 4–8 | 4 |
| Carbonate | 11–100 | 6–21 | 8–11 | 4 |

Table II shows that in most formations, the number of frequencies required to maximize snr is less than the current number of frequencies in commonly used tools such as the the MRIL prime tool (9 frequencies) of Numar Corporation. The exceptions are gas formations and some light oil reservoirs having a high gas/oil ratio. In other cases, a substantial improvement in snr can be realized by designing an acquisition scheme that utilizes all tool frequencies. The improvement ranges from 0% for gas and some light oil reservoirs up to 73% in heavy oil reservoirs.

The need for a different acquisition arises when the formation fluid properties dictate a long AT and a short TW. More frequencies can be used to improve the SNR where it is needed most—at the beginning of the echo train. One method for doing this is to include in the acquisition a series of pulse sequences with shorter acquisition times, but with the same TE and $T_W$. This can be demonstrated by considering the contribution to the echo amplitude by individual components of the formation fluids. For fluid component l, the echo amplitude at time $t_n$=nTE for echo train m is $$e_{lm}(t_n) = A_l \exp\left\{-\frac{t_n}{T_{2l}}\right\} \exp\left\{-\frac{1}{12}(\gamma GTE)^2 D_l t_n\right\}\left(1 - \exp\left\{-\frac{T_{Wm}}{T_{1l}}\right\}\right),$$

where $A_l$ is the amplitude of fluid component signal; $T_{il}$ are the fluid relaxation times; $D_l$ is the fluid diffusion constant; and $T_{Wm}$ is the wait time for the echo train (or frequency) m. The remaining symbols have their usual NMR meaning. The fluid component is any fraction of the earth formation fluids. This includes natural gas, oil or some component thereof, and formation water where the index indicates different pore sizes and hence different relaxation times. This expression can be summed over the fluid component to yield the total echo amplitude.

$$E_m(t_n) = \sum_l e_{lm}(t_n) + N_n$$

$$= \sum_l \left(A_l \exp\left\{-\frac{t_n}{T_{2l}}\right\} \exp\left\{-\frac{1}{12}(\gamma GTE)^2 D_l t_n\right\}\left(1 - \exp\left\{-\frac{T_{Wm}}{T_{1l}}\right\}\right)\right) + N_n.$$

The signal that is finally detected is then the echo amplitude plus the thermal noise signal.

In the above equation, $N_n$ is the noise signal and is assumed to be independent of the frequency of the measurement. If TE and $T_W$ are kept constant the, the total echo amplitude depends only on the echo number n or $t_n$. As a consequence the detected signal can be averaged over the echo trains.

$$S(t_n) = \langle S_m(t_n) \rangle$$

$$= \sum_l \left(A_l \exp\left\{-\frac{t_n}{T_{2l}}\right\} \exp\left\{-\frac{1}{12}(\gamma GTE)^2 D_l t_n\right\}\left(1 - \exp\left\{-\frac{T_W}{T_{1l}}\right\}\right)\right) + \langle N_n \rangle,$$

where the noise signal depends on the echo index. $T_{Wm}$ is replaced by $T_W$ because it is now a constant. Before averaging the noise has a certain RMS value, and after averaging the RMS value is smaller by the square root of the number of echo signals averaged together. Because the echo trains are different lengths, echoes with small n may have more echo signals averaged together than those with large n. Thus a single echo train is created in which the SNR varies from one datum to the next. This is an advantage because echo train can be inverted with the standard inversion schemes. The industry would, in all likelihood accept constant resolved $T_2$ acquisitions more readily than the generalized case where both AT and $T_W$ become variables.

The restriction that $T_W$ is constant can be relaxed under certain conditions. If spin-lattice relaxation times of the formation fluids are much less than $T_{Wm}$, $T_{Wm} \gg T_{1l}$, then $$(1-\exp\{-T_{Wm}/T_{1l}\}) \approx 1,$$

and the $E_m(t_n)$ is again independent of m and can be averaged over all the echo trains again producing a single echo train where the RMS noise varies from one datum to the next.

Another method for improving snr could use the "extra" tool frequencies with shorter ATs and shorter $T_W$s. This method is used by the MRIL clay-bound water acquisition. See Prammer et al(1996) and U.S. Pat. No. 6,005,389, to Prammer. The drawback here is that the processing scheme must be modified to include the $T_1/T_2$ ratio of the formation fluids U.S. Pat. No. 6,069,477 to Chen et al, U.S. Pat. No. 5,486,762, to Freedman and Morriss and Dunn (1998) and Dunn and LaTorraca(1999) have devised schemes to do this. The Prammer '389 solution is not suitable for the generalized case and Chen improves upon it. Solutions by Freedman and Dunn are sensitive to the $T_1/T_2$ ratio. Even these solutions may not be satisfactory. In the generalized case, there may be $T_2$ components where two or more fluids contribute a signal. In this case, more than one $T_1/T_2$ ratio would be needed. AT could be shortened and the number of frequencies increased, but then the long $T_2$ component would suffer because the decay curve is not well sampled.

The present invention is a method of acquisition of NMR data providing a constant resolution of the $T_2$ distribution. A number of acquisitions could be designed to improve the snr, but only one example of constant resolved $T_2$ acquisition is described.

In an article entitled "Quantitative Interpretation of NMR Relaxation Data" in the Journal of Magnetic Resonance, 1989, pp 134–152, Whitall and Mackay (1989) have shown that the resolvability of a component in a $T_2$ spectrum is proportional to the square root of the number of data points and also proportional to the SNR.

$$R \propto SNR\sqrt{N_E} \qquad (9)$$

where $N_E$ is the number of echoes used in the fitting procedure. The SNR is proportional to the square root of the number of averages $N_A$. The number of echoes $N_E$ important in fitting a particular component will be proportional to the $T_2$ of that component because it decays to zero in a time proportional to $T_2$. Thus, $N_E$ $T_2/T_E$. Using this information, eq. (9) gives $$R \propto SNR_0\sqrt{N_A T_2/T_E} \qquad (10)$$
$$\propto SNR_0\sqrt{N_A T_2},$$

where $SNR_0$ is the SNR for a single acquisition and $T_E$ is assumed to be. constant Thus, the resolvability varies as the square root of $T_2$ across a distribution. This is the reason why short $T_2$ components as encountered in clay-bound water are particularly difficult to observe with NMR logging tools. Eq. (10) also shows that resolvability is inversely proportional to the square root of $T_E$. Thus, resolvability increases as the echo spacing is decreased.

Constant resolvability thus leads to a requirement that $$N_A T_2 = k \qquad (11)$$

where k is a constant. An ideal acquisition system would thus vary the number of averages $N_A$ continuously across the $T_2$ spectrum. This is clearly impractical. A preferred embodiment of the invention fixes the resolvability at a finite number of points.

Figure 3:
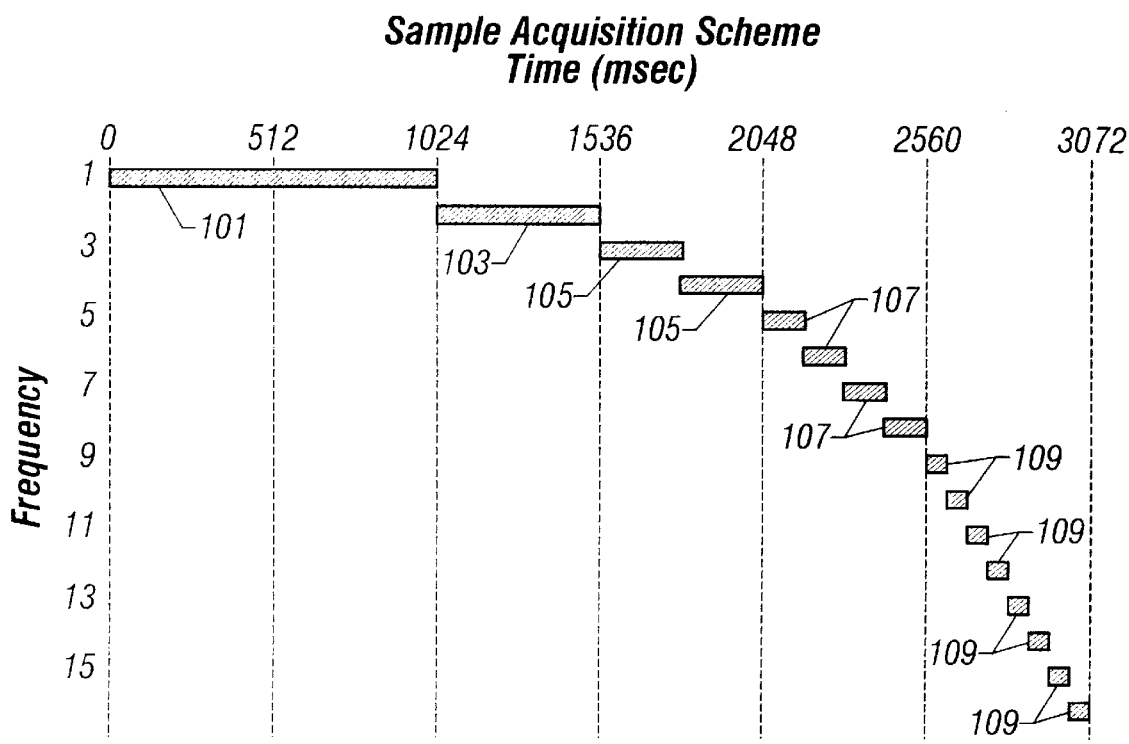
FIG. 3 shows an example of an acquisition scheme according to the present invention.

An example of such a scheme is illustrated in FIG. 3 wherein sixteen frequencies are used. The acquisition times at the frequencies 101, 103, 105, 107 and 109 are in the ratio of 16:8:4:2:1. The number of frequencies with the corresponding acquisition times is in the ratio 1:1:2:4:8.

The repetition time for a prior art acquisition is $TR_0 = 16$ $AT_0$ where $AT_0$ is the acquisition time at the first frequency. The repetition time for the acquisition sequence of FIG. 3 is given by $$TR' = 1AT_0 + 1\frac{AT_0}{2} + 2\frac{AT_0}{4} + 4\frac{AT_0}{8} + 8\frac{AT_0}{16} \qquad (12)$$

In general, $$TR' = AT_0\left(1 + \sum_{n=1}^{N_{aT}-1} \frac{1}{2}\right) \qquad (13)$$
$$= 3AT_0$$

where $N_{AT}$ is the number of different acquisition times. In this example, $N_{AT}$ five. For this example, the SNR of the constant resolved $T_2$ acquisition is an improvement by a factor of 2.3 over prior art fixed AT acquisition.

Figure 4:
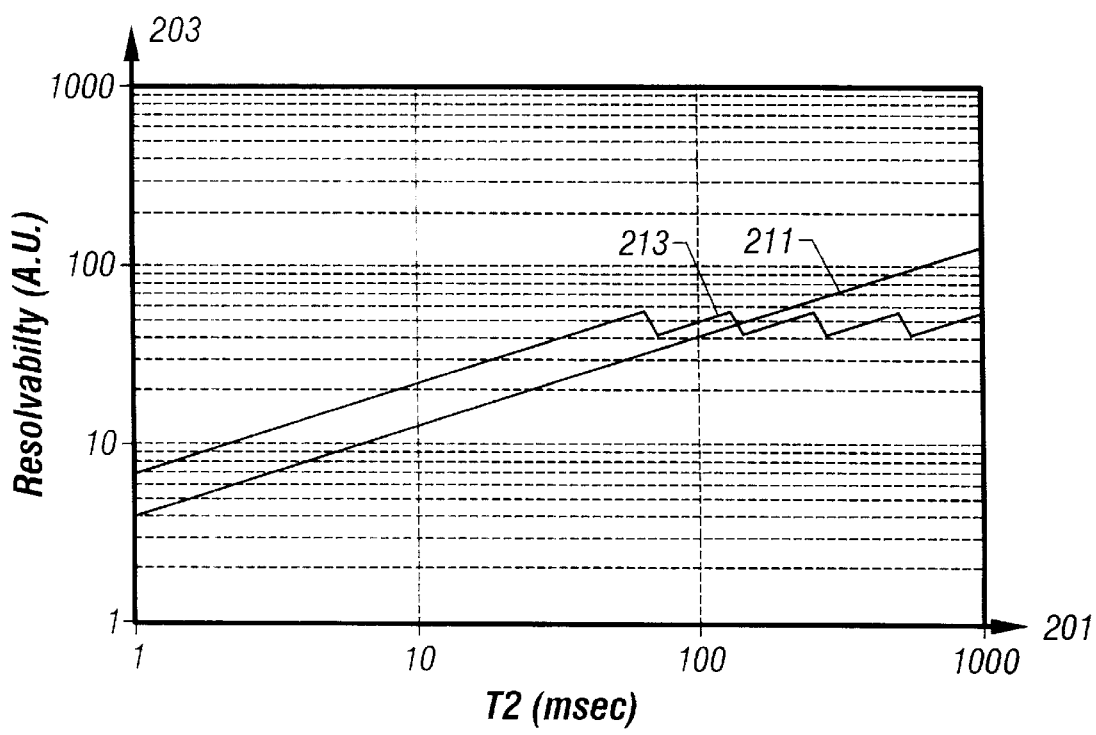
FIG. 4 shows a comparison of the resolvability of an acquisition scheme according to the present invention with a standard acquisition.

Turning now to FIG. 4, a comparison between a standard acquisition 211 and a constant resolved acquisition 213 using a 16-frequency tool is shown. The comparison is done using a fixed acquisition time. The abscissa 201 is the value of $T_2$ while the ordinate 203 is its resolvability. In this example the resolvability is improved for T2 <128 msec. It is decreased for T2>128 msec. The reduction is acceptable because resolvability is large in this region compared to T2<10 msec.

The present invention may also be used when a fixed wait time $T_W$ is desired. With prior art acquisition methods, all the frequencies could be used if $AT_0$ is shortened to a value consistent with constant pulsing. Alternatively, prior art methods could reduce the number of frequencies to accommodate the desired $AT_0$. Using, For example, if a $T_W$ of 7 seconds and an AT of one second are desired, eight frequencies may be used to acquire the data. Using the method of the present invention all sixteen freqeuncies may be used with a 40% improvement in snr. Alternatively, sixteen frequencies could be used in prior art methods and AT shortened to 0.5 seconds, but the resolvability of long $T_2$ components would suffer.

Figure 5A:
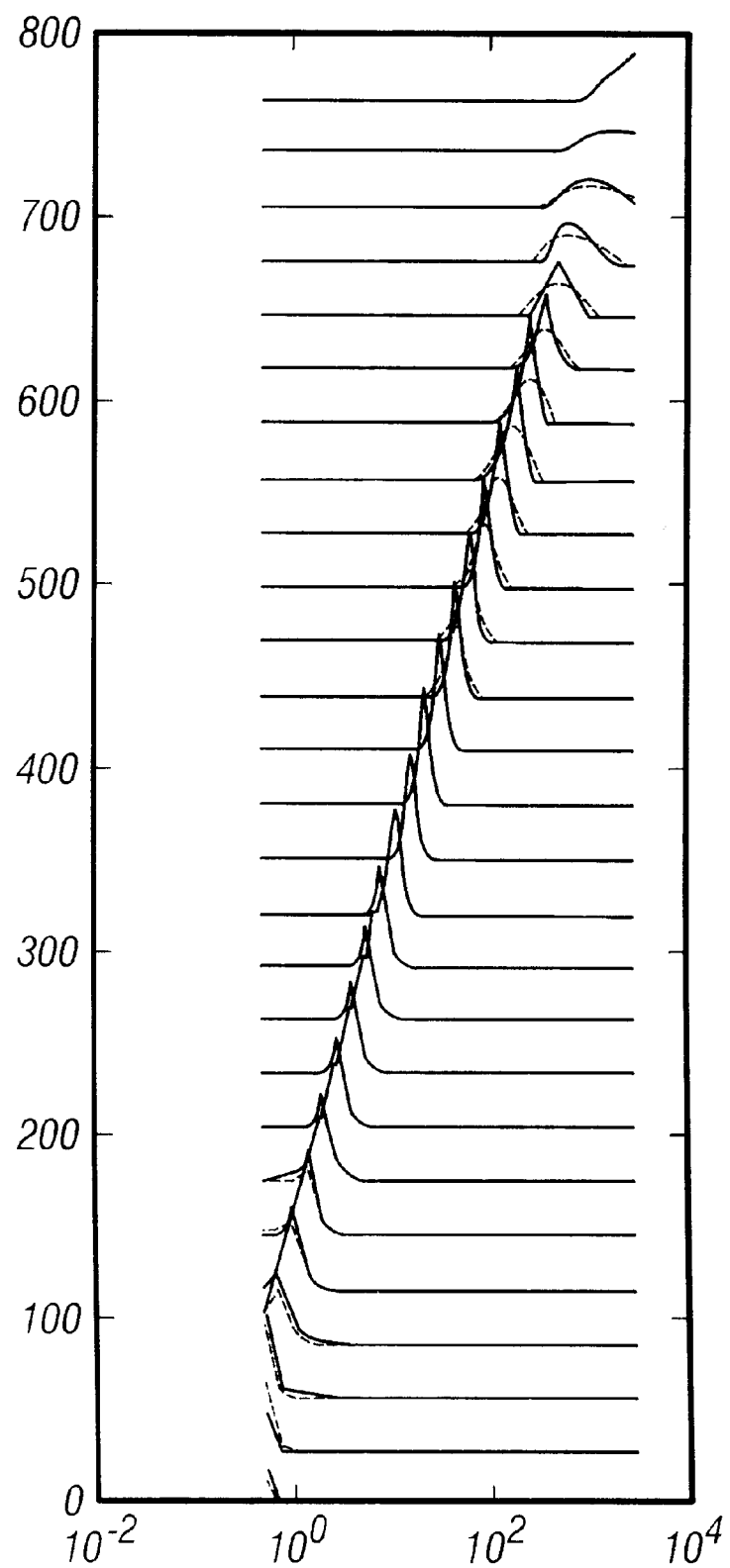
FIG. 5A shows an example of inversion of NMR data using the method of the present invention and a standard acquisition.
Figure 5B:
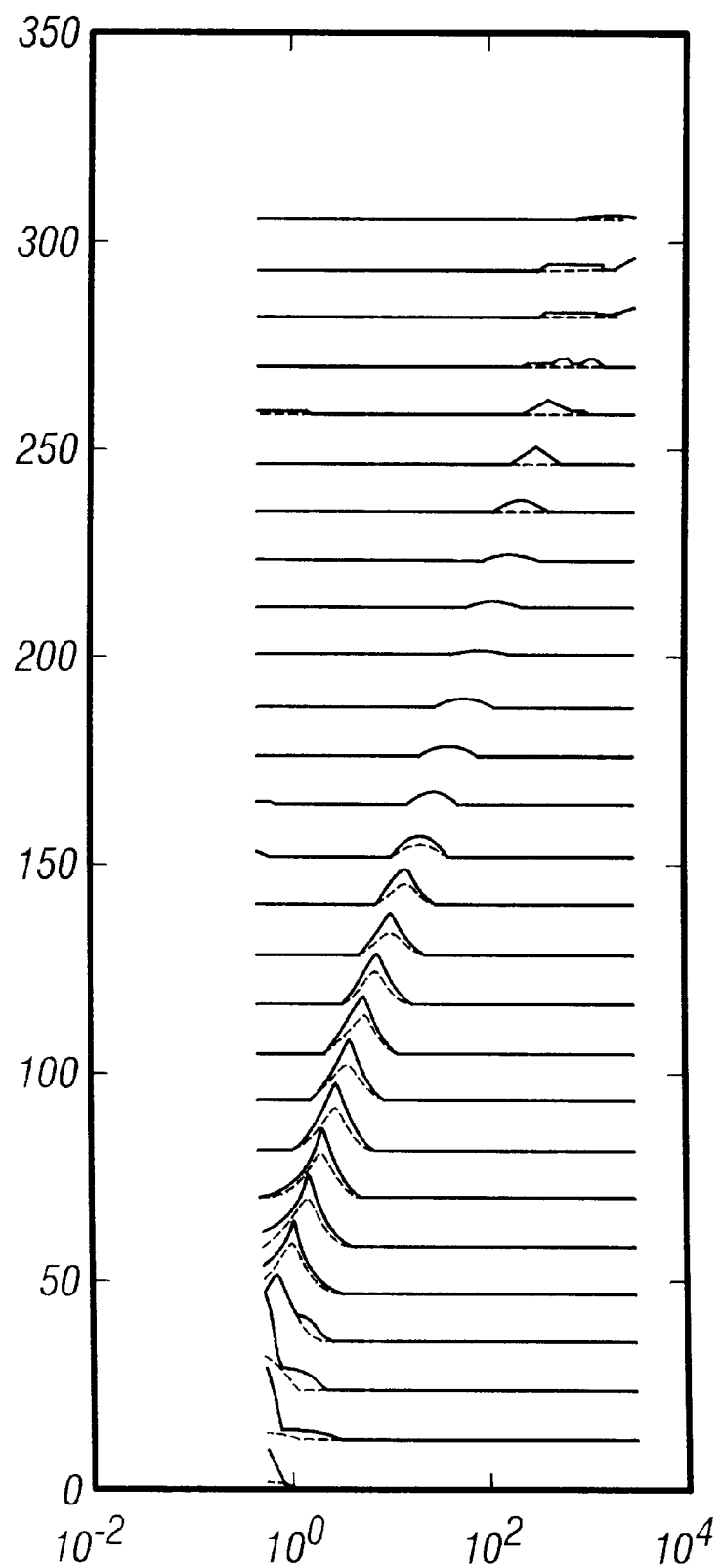
FIG. 5B shows the standard deviation of the inversion results for the NMR data inversion shown in FIG. 5A.

FIGS. 5A and 5B show examples of the results of using the method of the present invention on synthetic data. Simulations of NMR data were made using a single exponential function with a value of $T_2$ ranging from 0.25 ms. to 2048 ms One hundred simulations were performed using either the standard CPMG sequence or the constant resolved $T_2$ acquisition. The parameters used are shown in Table III.

TABLE III

Acquisition parameters for single-exponential acquisitions

|  | Constant resolved $T_2$ 1:1:2:4:8 | Standard CPMG |
|---|---|---|
| AT | 1000 ms. (maximum) | 500 ms |
| $T_R$ | 4000 ms. | 4000 ms |
| NE | 2000 (maximum) | 1000 |
| Regularization | 0.128 | 0.5 |

The data were then inverted using singular value decomposition (Prammer 1995)and the obtained values of $T_2$ are shown in FIG. 5A with solid lines for the standard method and the dashed lines for the constant resolved $T_2$ acquisition. FIG. 5B shows the standard deviation of the inverted values of $T_2$ for the 100 simulations.

In singular value decomposition, singular values smaller than some threshold are typically set to zero before the inversion is completed. This smooths the solution. A threshold value that is too small will result in unstable results, while a threshold that is too large will smooth out features of the solution. The solution will not represent the underlying $T_2$ distribution in either case. Practically, the threshold is typically set just large enough that the solution remains stable and therefore minimally smoothed. The threshold for this example is shown in table III as the regularization parameter.

It may be seen in FIG. 5A that the constant resolved $T_2$ acquisition reproduces the single exponential at small $T_2$ better than the standard acquisition, but poorer at large $T_2$ Better resolvability at the small $T_2$ is to be expected because this is precisely where the constant resolved $T_2$ acquisition is supposed to be better. At large $T_2$, the standard acquisition shows better resolution because the SNR for the echoes at the end of the echo train is larger than that of the constant resolved $T_2$. It is interesting to note that the last two echo trains with $T_2$ values of 2048 and 1448 are indistinguishable. This indicates that the resolvability of components with $T_2$ much larger that the acquisition time is about the same for both types of acquisitions.

The main benefit of the constant resolved $T_2$ is illustrated in FIG. 5B. Shown therein are the standard deviations for the standard acquisition (solid lines) and the constant resolved $T_2$ acquisition (dashed lines). It shows that the precision of the constant resolved $T_2$ measurement is better that the standard acquisition for almost all values of $T_2$. This is true even though the regularization parameter is smaller than the standard acquisition. The constant resolved $T_2$ acquisition will produce a smoother log when used because of the increased precision.

The above embodiment of the invention has been described with reference to the use of CPMG sequences for making the pulse echo measurements. U.S. Pat. 6,163,153 to Reiderman et al, having the same assignee as the present application and the contents of which are fully incorporated herein by reference, teaches the use of a modified CPMG sequence. The initial tipping pulse in this modified CPMG sequence tips the nuclear magnetic spins by about 90° relative to their alignment with the applied static filed; however, the subsequently applied refocusing pulses have a tip angle that is less than 180°. Refocusing pulses having a tip angle between 80° and 120° are shown to have an improved signal to noise ratio relative to a conventional CPMG sequence with refocusing pulses having a 180° tip angle while consuming substantially the same electrical power. One embodiment of the present invention uses such modified CPMG sequences having a refocusing angle of less than 180°.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method of nuclear magnetic resonance measurement of a medium, comprising:
    (a) magnetically polarizing nuclei in said medium with a static magnetic field;
    (b) acquiring a first CPMG echo train from a first sensitive volume, said first echo train having a first duration;
    (c) defining a second duration less than the first duration and a third duration less than the second duration; and
    (d) acquiring a plurality of additional CPMG echo trains having sensitive volumes different from each other and from the first sensitive volume and having a duration that is one of the second duration and the third duration and wherein a product of the number of additional echo trains having the third duration and the third duration is substantially equal to or less than the second duration.

2. The method of claim 1 wherein the second duration is one half of the first duration, the third duration is one half of the second duration and wherein the plurality of additional echo trains is at least three, said additional echo trains comprising:
    (i) one echo train having the second duration, and
    (ii) two echo trains having the third duration.

3. The method of claim 2 further comprising acquiring four additional CPMG echo trains having a fourth duration that is one half of the third duration.

4. The method of claim 3 further comprising acquiring eight additional CPMG echo trains having a fifth duration that is one half of the fourth duration.

5. The method of claim 1 wherein each different sensitive volume is associated with a different radio frequency of the associated CPMG echo train.

6. The method of claim 1 wherein doubling the number of sensitive volumes increases a signal-to-noise ratio per root time by between 35% and 45%.

7. The method of claim 1 wherein the first duration is related to a maximum transverse relaxation time of a fluid in the formation.

8. The method of claim 1 wherein the medium does not contain gas or light oil and wherein the number of different sensitive volumes is less than 10.

9. The method of claim 1 wherein the durations and pluralities of additional echo trains are selected to give a constant resolvability of a $T_2$ spectrum of the formation.

10. A method of nuclear magnetic resonance measurement of a medium, comprising:
    (a) magnetically polarizing nuclei in said medium with a static magnetic field;
    (b) selecting a first plurality of different sensitive volumes;
    (c) for each of said plurality of sensitive volumes, acquiring an associated CPMG echo train having an associated duration, said associated durations of said associated CPMG echo trains selected to give a substantially constant resolvability of a $T_2$ spectrum of said medium.

11. The method of claim 10 wherein the plurality of sensitive volumes is at least four, and wherein the associated durations are in the ratio of 1.0, 0.5, 0.25 and 0.25 respectively.

12. The method of claim 10 wherein the plurality of sensitive volumes is at least seven, and wherein the associated durations are in the ratio of 1.0, 0.5, 0.25, 0.25, 0.125, 0.125, 0.125 and 0.125 respectively.

13. The method of claim 10 wherein each of the plurality of sensitive volumes is associated with a different radio frequency of the associated CPMG echo trains.

14. The method of claim 10 wherein the duration associated with the first of the plurality of sensitive volumes is related to a maximum transverse relaxation time of a fluid in the formation.

15. The method of claim 10 wherein the medium does not contain gas or light oil and wherein the number of different sensitive volumes is less than 10.

16. A method of nuclear magnetic resonance measurement of a medium, comprising:
    (a) magnetically polarizing nuclei in said medium with a static magnetic field;
    (b) acquiring a first echo train from a first sensitive, said first echo train having a first duration;
    (c) defining a second duration less than the first duration and a third duration less than the second duration; and
    (d) acquiring a plurality of additional echo trains having sensitive volumes different from each other and from the first sensitive volume and having a duration that is one of the second duration and the third duration and wherein a product of the number of additional echo trains having the third duration and the third duration is substantially equal to or less than the second duration;
    wherein at least one of the first echo train and the additional echo trains comprises a modified CPMG sequence having a refocusing angle less than 180°.

17. The method of claim 16 wherein each different sensitive volume is associated with a different radio frequency of the associated echo train.

18. A method of nuclear magnetic resonance measurement of a medium, comprising:
    (a) magnetically polarizing nuclei in said medium with a static magnetic field;
    (b) selecting a first plurality of different sensitive volumes; and (c) for each of said plurality of sensitive volumes, acquiring an associated echo train having an associated duration, said associated durations of said associated echo trains selected to give a substantially constant resolvability of a $T_2$ spectrum of said medium;

wherein at least one of said echo trains comprises a modified CPMG sequence having a refocusing angle less than 180°.

19. The method of claim 18 wherein the plurality of sensitive volumes is at least four, and wherein the associated durations are in the ratio of 1.0, 0.5, 0.25 and 0.25 respectively.

20. The method of claim 18 wherein the plurality of sensitive volumes is at least seven, and wherein the associated durations are in the ratio of 1.0, 0.5, 0.25, 0.25, 0.125, 0.125, 0.125, and 0.125 respectively.

21. The method of claim 18 wherein each of the plurality of sensitive volumes is associated with a different radio frequency of the associated echo trains.

22. The method of claim 18 wherein the duration associated with the first of the plurality of sensitive volumes is related to a maximum transverse relaxation time of a fluid in the formation.

* * * * *